United States Patent [19]
Warncke et al.
[11] 4,275,723
[45] Jun. 30, 1981

[54] WARNING DEVICE FOR BREATHING APPARATUS HAVING A PRESSURE GAS SUPPLY

[75] Inventors: Ernst Warncke, Lübeck; Adalbert Pasternack, Bad Schwartau, both of Fed. Rep. of Germany

[73] Assignee: Drägerwerk Aktiengesellschaft, Fed. Rep. of Germany

[21] Appl. No.: 68,668

[22] Filed: Aug. 22, 1979

[30] Foreign Application Priority Data

Sep. 2, 1978 [DE] Fed. Rep. of Germany ....... 2838366

[51] Int. Cl.³ ............................................ A61M 16/00
[52] U.S. Cl. .......................... 128/202.22; 128/205.24; 137/557; 116/24; 116/70; 116/137 R
[58] Field of Search ...................... 128/202.22, 205.23, 128/205.24; 116/24, 67 R, 70, 112, 137 R; 137/557; 91/1, 38, 165; 92/49

[56] References Cited

U.S. PATENT DOCUMENTS

| | | | |
|---|---|---|---|
| 3,719,160 | 3/1973 | Christianson | 116/70 |
| 3,785,333 | 1/1974 | Warncke et al. | 116/70 |
| 3,896,837 | 7/1975 | Rohling | 128/202.22 X |

FOREIGN PATENT DOCUMENTS

| | | | |
|---|---|---|---|
| 1133251 | 7/1962 | Fed. Rep. of Germany | 128/202.22 |
| 2129529 | 7/1975 | Fed. Rep. of Germany | 128/202.22 |

*Primary Examiner*—Charles N. Hart
*Assistant Examiner*—David R. Sadowski
*Attorney, Agent, or Firm*—McGlew and Tuttle

[57] ABSTRACT

A warning device for breathing apparatus which has a respiratory gas conduit through which respiratory gases are passed and which includes three interconnected chambers. Two of the chambers include diaphragm valves operable, responsive to pressure conditions therein, to actuate a piston in the third chamber which moves a signaling element into the gas conduit to signal a low pressure condition.

4 Claims, 1 Drawing Figure

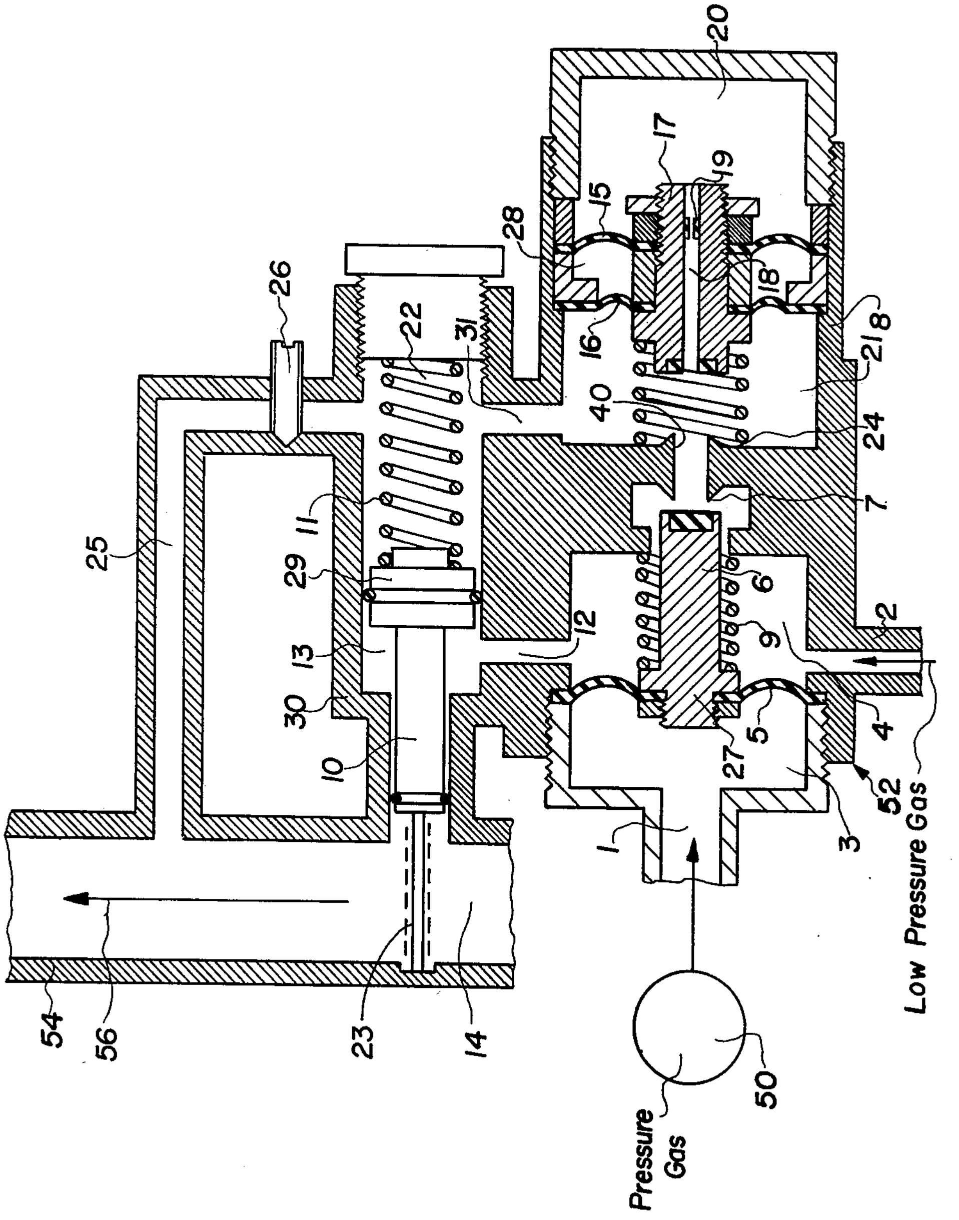
Low Pressure Gas
Pressure Gas
1
2
3
4
5
6
7
9
10
11
12
13
14
15
16
17
18
19
20
21
22
23
24
25
26
27
28
29
30
31
40
50
52
54
56

WARNING DEVICE FOR BREATHING APPARATUS HAVING A PRESSURE GAS SUPPLY

FIELD AND BACKGROUND OF THE INVENTION

This invention relates in general to respirating devices and in particular to a new and useful warning device for a respirator having a pressure gas supply.

It is absolutely necessary for the user of a protective breathing apparatus with a pressure gas supply, to know in advance whether breathing gas will be supplied at all, and to be warned in time if the pressure gas supply is exhausted.

Prior art warning devices may signal either a residual pressure or the fact that the cylinder valve is not open or that the cylinder is empty.

A known warning device for protective breathing apparatus with pressure gas supply uses a combination of these two possibilities and provides a whistle as the signalling element which, upon opening the shut-off valve of the pressure gas supply, produces a short whistle as a checking signal indicating the readiness of the warning device, and then is actuated again for short periods of time to indicate that the pressure in the pressure gas tank dropped below a predetermined value and the gas is going to be exhausted.

This prior art warning device comprises a first pressure controlled diaphragm valve which is controlled to close under high pressure, and to open under a medium pressure and a spring force. As the high pressure drops below a desired threshold value, the open forces prevail and the first diaphragm valve opens. This enables the medium pressure to reach the signalling element, through a connecting passage and a second diaphragm valve which is designed as a pressure controlled double diaphram valve, and thus to produce the warning signal.

To minimize the pressure gas consumption, the warning time period is limited by the second diaphragm valve. In its normal position, the second diaphragm valve is open under the action of a spring. Its control members are two diaphragms and a valve-closing body secured thereto. One diaghragm has a smaller surface area and is exposed to the pressure in the connecting passage, while the other diaphragm, having a larger surface area, forms a boundary of a completely enclosed space and is exposed to the pressure which is produced in this space by the gas penetrating therein through a bore and a throttle in the valve body.

Due to the unequal surface areas of the diaphragms, the second diaphragm valve closes as the closing pressure is reached and shuts off the gas stream to the signalling element. What is disadvantageous in this warning device is the absence of a warning signal if the gas cylinder is not open or entirely empty, and a certain gas loss caused by the warning signal if the pressure drops below the threshold value (German Pat. No. 21, 29, 529).

SUMMARY OF THE INVENTION

The invention is directed to a warning device which is applicable to any protective breathing apparatus with pressure gas supply and warns the user both if the pressure gas tank is not open or empty, and upon reaching a residual pressure, with the warning requiring only a very small gas amount which is not lost for the respiratory circuit.

In accordance with the invention a warning device is connected to the respiratory gas conduit and it comprises a warning piston having a warning signal which is moved by the piston into the conduit so as to be actuated thereby during respiratory gas flow therethrough. The movement of the piston is controlled by two diaphragm valves, the first including a diaphragm which divides a housing chamber into a high pressure space which is connected to the pressure gas supply and a low pressure space which is connected to a low pressure line. This first diaphragm valve is connected through a chamber to the high pressure side or vestibule space of a second diaphragm valve. The low pressure space of the first diaphragm valve is connected to one end of the warning piston chamber in which the warning piston is movable and the vestibule space of the second diaphragm valve is connected to the warning piston chamber on the opposite side of the piston from the first connection. In addition this same side of the warning piston chamber is connected to the respiratory gas conduit. In the pressure-less state or with the pressure dropping below the resdidual pressure, the signalling element is moved into the respiratory path and the warning device is actuated by the movement of the respiratory gases.

With the invention, a simple, reliable warning device is obtained which is rugged in construction and requires only a small amount of breathing gas which is then completely returned into the breathing circuit. The design with the first connecting passage from the space of the first diaphragm valve and the second connecting passage from the vestibule of the second diaphragm valve provides a sensitive control of the movement of the warning piston with the signalling element. With the valve of the pressure gas tank, for example, pressure gas cylinder, closed, of after a complete exhaustion, the two connecting passages are under normal pressure. The warning system is not exposed to any differential pressure. The compression spring displaces the warning piston in the direction of, and thereby the signalling element into the respiratory path. Depending on the employed signalling element, the user perceives an acoustic signal or a strongly increased resistance to breathing. He is thus warned that the pressure gas tank is not open or empty.

If the protective breathing apparatus is used with a satisfactory breathing gas supply, made evident by a high pressure in the pressure gas tank, the low-pressure gas can flow through the first connecting passage, but not through the second connecting passage, since the first diaphragm valve is then closed. The low-pressure gas having passed through the first connecting passage, displaces the warning piston against the action of the spring, so that the signalling element is withdrawn from the respiratory path. The user can respire freely. His respiration does not cause any acoustic signal and is not obstructed by any increased resistance.

As the residual pressure is reached during use, the first diaphragm valve opens, this enables the low-pressure gas to flow also through the second connecting passage. Upon pressure equalization at both sides of the warning piston, the spring displaces the signalling element into the respiratory path, in the already known manner. The user is being warned. The warning is limited in time. The warning time period is determined by the second diaphragm valve which closes after the pressure equalization and thereby prevents the low-pressure gas from flowing into the space behind the warning piston. The pressure in this space drops, because the low-pressure gas expands through the third connecting passage into the respiratory path, whereupon the low-pressure gas displaces the warning piston in the direction opposite to the action of the spring and the warning signal is stopped.

The warning time period can be varied by means of the adjustable throttle in the third connecting passage.

Accordingly, it is an object of the invention to provide an improved warning device in which a signal member is moved into a respiratory gas conduit for actuation by the gases moving therethrough under the control of a valve which is connectable to a high-pressure gas supply and the time for the signal is regulated by movement of the piston backwardly under the control of second diaphragm valve.

A further object of the invention is to provide a warning device, which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the Drawing:

FIG. 1 is partly schematic sectional view of a warning device for breathing apparatus having a pressure gas supply constructed in accordance with the invention.

DESCRIPTION OF THE PREFERRED EMBODIMENT

Referring to the drawing, in particular, the invention embodied therein comprises a warning device for breathing apparatus which has a pressure gas supply 50 which is connected to a housing generally designated 52 of a breathing apparatus which includes a conduit 54 defining a respiratory gas flow path 14. The respiratory gases flow in an inhaling direction as indicated by the arrow 56 and in a reverse flow by expiration of the patient.

The signalling element of the invention advantageously comprises vibrating reeds which fill the cross-section of the conduit 54 and provide either an acoustic signalling element or an element which increases the resistance in the respiratory path in the direction of the arrow 56. Both types of signals will be perceived by the user reliably. The inventive solution ensures a quite satisfactory warning of the user both as to the breathing gas supply tank being opened or closed or upon reaching a residual pressure.

The warning device is connected, by means of a connection 1, to the high-pressure line, and by means of a connection 2, to a low-pressure line of a pressure reducer of a protective breathing apparatus, and thus also to the oxygen supply tank. Upon opening the cylinder valve of the oxygen supply tank, the oxygen flows under high pressure through connection 1 into the high pressure space 3 of a first diaphragm valve 27. At the same time, low-pressure oxygen passes from the pressure reducer (not shown) through connection 2 into the low-pressure space 4 of first diaphragm valve 27. Due to the differential pressure between high-pressure space 3 and low-pressure space 4, which are separated from each other by the diaphragm 5 of the valve, valve member or valve piston 6 is pressed against a crater-like seat 7, whereby first diaphragm valve 27 is closed and the low-pressure oxygen is prevented from flowing into a the control part 8 of the warning device, accommodating a second diaphragm valve 28.

First diaphragm valve 27 remains closed as long as the high pressure exceeds the sum of the low pressure and the force of a spring 9.

Second diaphragm valve 28 comprises two diaphragms 15 and 16, having unequal surface areas and connected to each other by a valve piston 17. A bore 18 in valve piston 17, in which a throttle 19 is received, provides communication between a vestibule space 21 and a rear space 20. An orifice 40 interconnects the low pressure space 4 and the vestibule space 21. As soon as the pressure in spaces 20 and 21 become equal to each other, valve body 17 is pressed against a crater-like seat 24, due to the larger surface area of diaphragm 15, and second diaphragm valve 28 is closed.

Warning device 29 comprises a warning piston 10 accommodated in a compartment in a housing 30. The piston is urged by a spring 11 in the direction of the respiratory gas flow path 14. On that end of the piston, a signalling element 23 is provided. The space 13 in front of warning piston 10 is connected thorugh a first connecting passage 12, to the low pressure space 4, and space 22 behind warning piston 10 is connected through a second connecting passage 31, to the vestibule 21 of second diaghragm valve 28. Space 22 is further connected, through a third connecting passage 25, to the respiratory gas flow path 14. An adjustable throttle 26 is received in third connecting passage 25.

With the cylinder valve of the oxygen supply tank closed, or with the oxygen supply tank empty, normal pressure is present in connecting passages 12 and 31. Spring 11 urges warning piston 10 in the direction of respiratory path 14 and, thereby, signalling element 23 into this path. Signalling element 23 is designed with vibrating reeds, so that an acoustic signal is produced during respiration. This signal is to remind the user that the valve is not open or that the supply of pressure-oxygen is almost exhausted.

With the opening of the cylinder valve, first diaphragm valve 27 closes. The low-pressure gas flows through low-pressure space 4 and first connecting passage 12 into space 13 and displaces warning piston 10 against the action of spring 11 whereby signalling element 23 is simultaneously withdrawn from respiratory path 14. The warning is stopped. The user of the apparatus knows that the oxygen supply tank is open and that the pressure is satisfactory. As soon as, in service, only residual pressure remains in the oxygen supply tank, first diaphragm valve 27 opens. Thereby, the low pressure is applied through both connecting passages 12 and 31 to warning piston 10. Spring 11 pushes the piston in the direction of respiratory path 14. Signalling element 23 is again moved into the path and the respiration produces a sound, warning the user. As the pressures in vestibule 21 and rear space 20 become equalized, second diaphragm valve 28 closes at crater-like seat 24. This interrupts the flow of low-pressure gas through second connecting passage 31 into space 22. After the gas pressure in space 22 drops, due to the expansion through third connecting passage 25, signalling element 23 is withdrawn again from respiratory path 14 and the warning limited in time is stopped. This warning-time period results from the adjustment of the throttle 19 and a throttle 26 in third connecting passage 25.

While a specific embodiment of the invention has been shown and described in detail to illustrate the application of the principles of the invention, it will be understood that the invention may be embodied otherwise without departing from such principles.

What is claimed is:

1. A warning device for a protective breathing gas apparatus of the type having a high pressure gas supply and a pressure reducer connected to the high pressure gas supply for providing a low pressure gas supply comprising a conduit defining a respiratory gas flowpath, a housing having a first chamber, first diaphragm valve means mounted in said first chamber and dividing said first chamber into a high pressure space connected to the high pressure gas supply and a low pressure space connected to the low pressure gas supply, said first diaphragm valve means being movable responsive to the differential pressure between said pressure spaces, a second chamber, second diphragm valve means movably mounted in said second chamber dividing said second chamber into a vestibule space and a rear space and including a bore connecting said vestibule space and said rear space, wall means defining an orifice for connecting said low pressure space and said vestibule space and including a first valve seat adjacent said low pressure space for sealingly receiving said first diaphragm valve means and a second valve seat adjacent said vestibule space for sealingly receiving said second diaphragm valve means, a third chamber having a piston compartment in fluid communication with the gas flowpath, a piston slidably mounted in said piston compartment and dividing said piston compartment into a first piston space communicating with said flowpath and a second space, said piston having a signal portion movable with said piston between a first portion into the flowpath and a second position out of the flowpath, said signal portion being responsive to fluid flow in said flowpath for actuating a warning signal, a first passage connecting said low pressure space and said first piston space, a second passage connecting said vestibule space and said second piston space, a third passage connecting said second piston space and said flowpath, means for throttling said third passage, said first diaphragm valve means being operative to sealingly engage said first valve seat when the differential pressure is above a predetermined level and to sealingly disengage from said first valve seat when the differential pressure is below the predetermined level, said second valve means being operative to sealingly engage said second valve seat when the pressure in said vestibule space and said rear space is equal, and said piston being operative to move the signal portion into the flowpath when said first diaphragm valve means and said second diaphragm valve means are respectively disengaged from said first valve seat and said second valve seat.

2. A warning device according to claim 1, wherein said signal portion comprises a vibrating reed.

3. A warning device according to claim 1, wherein said first diaphragm valve means comprises a diaphragm portion movably mounted to the housing portion defining said first chamber and a first valve member connected to said diaphragm portion in said low pressure space adapted to sealingly engage said first valve seat, and a spring mounted to said housing in said low pressure space for biasing said first valve member away from said first valve seat.

4. A warning device according to claim 3, wherein said second diaphragm valve means comprises a second valve member adapted to sealingly engage said second valve seat, a second diaphragm portion and a third diaphragm portion movably mounted to the housing portion defining said first chamber and to said second valve member, said second diaphragm portion having surface area adjacent to said rear space, and said third diaphragm portion having a surface area adjacent to said vestibule space, said latter surface area is smaller than said former surface area, and a spring mounted to said housing in said vestibule space for biasing said second valve member away from said second valve seat.

* * * * *